(12) United States Patent
Imahashi et al.

(10) Patent No.: US 7,508,118 B2
(45) Date of Patent: Mar. 24, 2009

(54) ULTRASONIC TRANSDUCER

(75) Inventors: Takuya Imahashi, Kawasaki (JP);
Akiko Mizunuma, Tokyo (JP);
Yukihiko Sawada, Yoshikawa (JP);
Katsuhiro Wakabayashi, Tokyo (JP);
Sunao Sato, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/664,708

(22) PCT Filed: Sep. 29, 2005

(86) PCT No.: PCT/JP2005/017998

§ 371 (c)(1),
(2), (4) Date: Jun. 8, 2007

(87) PCT Pub. No.: WO2006/038525

PCT Pub. Date: Apr. 13, 2006

(65) Prior Publication Data

US 2008/0018206 A1  Jan. 24, 2008

(30) Foreign Application Priority Data

Oct. 5, 2004 (JP) ................................ 2004-292144

(51) Int. Cl.
*H01L 41/08* (2006.01)
(52) U.S. Cl. ..................................... 310/334
(58) Field of Classification Search ................. 310/322, 310/334
See application file for complete search history.

(56) References Cited

U.S. PATENT DOCUMENTS

| 4,385,255 | A |   | 5/1983  | Yamaguchi et al. |
|-----------|---|---|---------|------------------|
| 4,783,888 | A | * | 11/1988 | Fujii et al. ................. 29/25.35 |
| 5,764,596 | A | * | 6/1998  | Hanafy et al. ................ 367/153 |
| 6,020,675 | A | * | 2/2000  | Yamashita et al. ........... 310/358 |
| 6,306,199 | B1| * | 10/2001 | Gustafson et al. ............. 95/226 |
| 2004/0041497 | A1 |  | 3/2004 | Hamada et al. |

FOREIGN PATENT DOCUMENTS

| JP | 56-66992    | 6/1981  |
| JP | 59-20240    | 5/1984  |
| JP | 61-032698   | 2/1986  |
| JP | 62-210000   | 9/1987  |
| JP | 05-003598   | 1/1993  |
| JP | 2001-326997 | 11/2001 |
| JP | 2004-15767  | 1/2004  |

\* cited by examiner

*Primary Examiner*—Thomas M Dougherty
(74) *Attorney, Agent, or Firm*—Scully, Scott, Murphy & Presser, P.C.

(57) ABSTRACT

Disclosed is an ultrasonic transducer which is composed of a plurality of piezoelectric elements having an electrode on each of two opposite surfaces, an acoustic matching layer arranged on the first surface that is one of the two opposite surfaces, a wiring board so arranged on the acoustic matching layer as to be in contact with the piezoelectric element, and a conductor electrically connecting the wiring board with the electrode on the second surface that is one of the two opposite surfaces. This ultrasonic transducer is characterized in that the surface of the wiring board on the same side as the second surface of the piezoelectric element is positioned relatively lower than the second surface of the piezoelectric element.

7 Claims, 7 Drawing Sheets

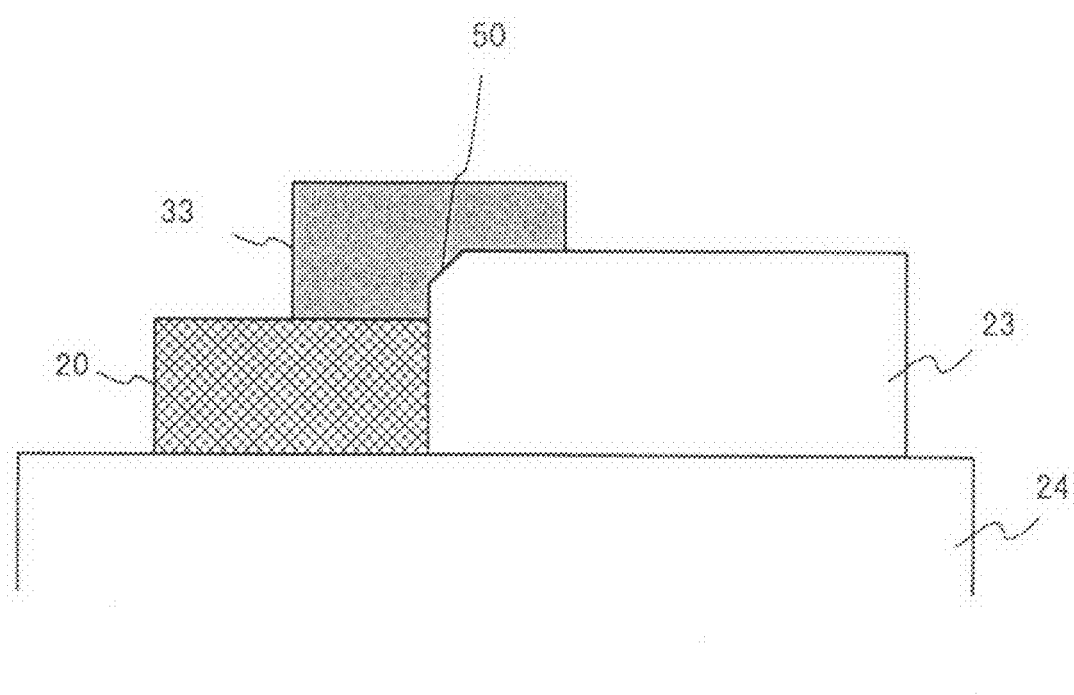
F I G. 6

ULTRASONIC TRANSDUCER

TECHNICAL FIELD

The present invention relates to an ultrasonic transducer which obtains an ultrasonic image by transmitting/receiving an Ultrasound in a body cavity.

BACKGROUND ART

An ultrasonic transducer, which is used for an ultrasonic diagnostic device, requires fine processing in its manufacturing, and a variety of manufacturing methods are conventionally proposed (for example, Patent Documents 1 and 2).

If an FPC (Flexible Print Circuit) is used as a wiring method for piezoelectric transducers, it is normal to partition the FPC by cutting it with a dicing saw after connecting the FPC to piezoelectric device (for example, Patent Document 1). Patent Document 1 discloses that improvements in stiffness, such as projecting an adhesive on the side of a piezoelectric device, are made to endure a load imposed when the FPC is cut with a dicing saw.

For a body-cavity ultrasonic transducer mounted in an ultrasonic endoscope, etc., its entire size must be reduced to a minimum, and a pain of a patient when an endoscope is inserted must be mitigated. Since the amount of an adhesive for improving stiffness cannot be stipulated with the shape disclosed by Patent Document 1, a size at the time of completion becomes large by an indefinite size, namely, an adhesive.

Especially, if FPC is bent along the side of a backing material, the remaining stress of the stiffness of the FPC becomes higher around piezoelectric elements so that the reliability of wires degrades. Additionally, Patent Document 1 describes that an FPC and piezoelectric transducers are glued. However, if soldering is used, it is difficult to control the amount of solder material. This leads to variations in the load mass of each piezoelectric transducer on vibrations after the FPC is cut down, which exert an influence on the ultrasound characteristic.

As disclosed by Patent Document 2, there is also an example where a conductive adhesive is used as a method other than soldering. According to Patent Document 2, a wiring board is provided on the side of a baching material, and the board and piezoelectric transducers are connected with a conductive adhesive.

However, it is difficult to control the amount of the conductive material to be coated on piezoelectric elements, and besides, the conductive adhesive is coated in an acoustic emission direction (=vibration direction). Therefore, the load mass of each piezoelectric transducer elements increases.

Patent Document 1: Japanese Published Unexamined Patent Application No. H5-3598
Patent Document 2: Japanese Published Examined Patent Application No. S59-20240

DISCLOSURE OF INVENTION

An object of the present invention is to provide an ultrasonic transducer of a small size, which does not interfere an improvement in reliability and the vibrations of a piezoelectric transducer, and suppresses variations in a characteristic.

The ultrasonic transducer according to the present invention comprises a plurality of piezoelectric elements having electrodes respectively on two opposed surfaces, an acoustic matching layer stacked on the side of a first surface that is one of the two surfaces, a wiring board which contacts the piezoelectric elements and is stacked on the acoustic matching layer, and a conductor which electrically connects the wiring board and the electrode on the side of a second surface that is one of the two surfaces, wherein the surface of the wiring board on the same side as the second surface of a piezoelectric element is positioned relatively lower than the second surface of the piezoelectric transducer.

Additionally, a method, according to the present invention, for manufacturing an ultrasonic transducer, which is configured with a plurality of piezoelectric transducers having electrodes respectively on two opposed surfaces, an acoustic matching layer stacked on the side of a first surface that is one of the two surfaces, a wiring board which contacts the piezoelectric transducers and is stacked on the acoustic matching layer, and a conductor which electrically connects the wiring board and the electrode on the side of a second surface that is one of the two surfaces, comprises: a piezoelectric transducer stacking step of stacking the piezoelectric device on the acoustic matching layer; a wiring board stacking step of stacking the wiring board, which is thinner than the piezoelectric element, on the surface of the acoustic matching layer and a side of a piezoelectric element; a masking step of masking a surface of the above structure, which is configured as a result of the wiring board forming step, other than a predetermined portion including a surface on which the piezoelectric transducer and the wiring board are glued; a conductor forming step of forming the conductor in a portion not masked by the masking step; and a masking removing step of removing the masked portion.

BRIEF DESCRIPTION OF DRAWINGS

FIG. 6 is a schematic showing a manufacturing process of an ultrasonic transducer configuring the inside of an ultrasonic transducer 10 in the third preferred embodiment.

BEST MODE OF CARRYING OUT THE INVENTION

Figure 1:
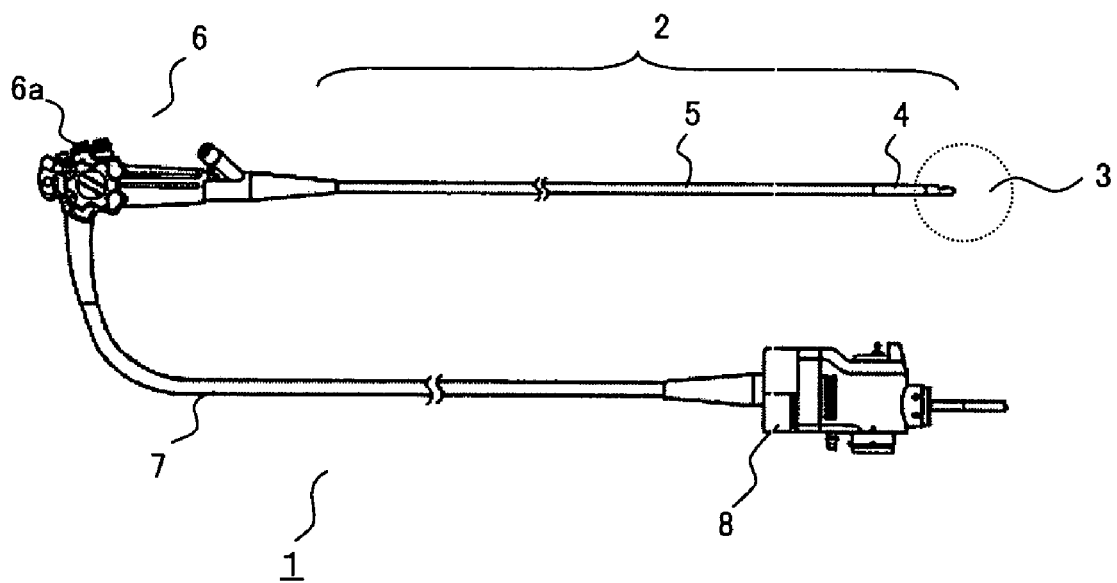
FIG. 1 is a schematic showing an configuration of an ultrasonic endoscope.

FIG. 1 shows an external configuration of an ultrasonic endoscope in a preferred embodiment of the present invention. The ultrasonic endoscope 1 comprises an control section 6 at the base end of a slender insertion tube 2, and a scope connector 8 at one end. From the side of the control section 6, a universal cord 7, which is connected to a light source device not shown, extends. Additionally, the scope connector 8 is connected to a diagnostic ultrasound system not shown.

The insertion tube 2 is configured by arranging a tip section 3, a bending section 4 that can freely bend, and a flexible tube section 5 having flexibility sequentially from the side of the tip. A angulation control knob 6a is provided in the control section 6. The angulation control knob 6a is operated, whereby the bending section 4 can be bent.

Figure 2:
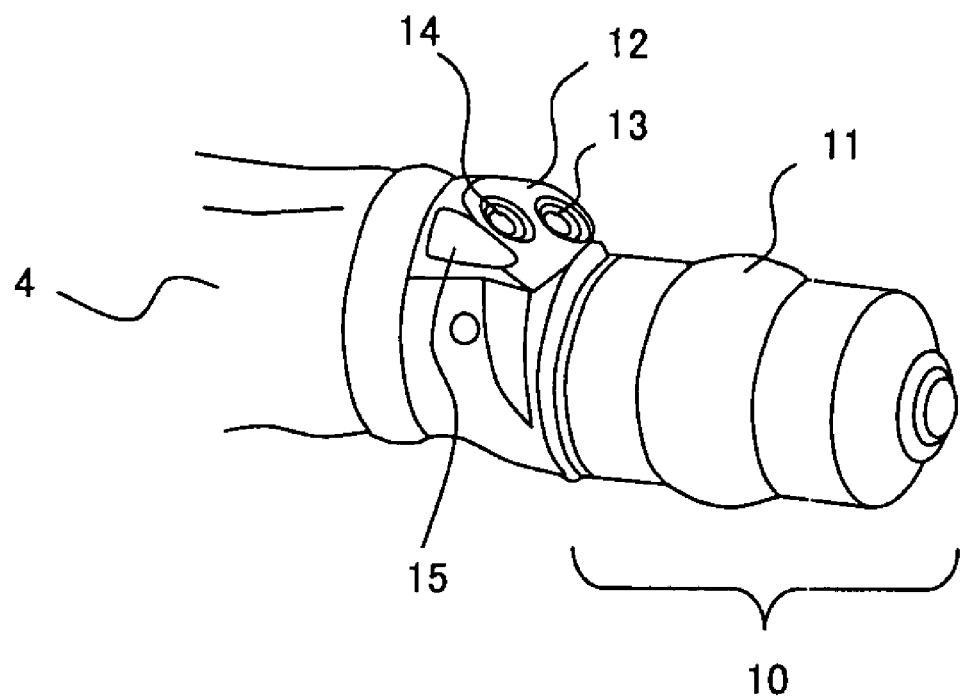
FIG. 2 is an detail of a tip section 3 of the ultrasonic endoscope 1 of FIG. 1.

FIG. 2 is an detail of the tip section 3 of the ultrasonic endoscope 1 of FIG. 1. At the tip section 3, an ultrasonic transducer 10 is provided, and a slope 12 is provided between the bending section 4 and the ultrasonic transducer 10. The ultrasonic transducer 10 is covered with a material of which an acoustic lens 11 is formed. Provided on the slope 12 are an light guide lens 14 configuring an illumination optics section for irradiating a portion to be observed with illumination light, an objective lens 13 configuring an observation optics section for capturing the optical endoscopic image of the portion to be observed, and a instrument channel outlet 15, which is an opening from which a therapeutic instrument appears.

Figure 3:
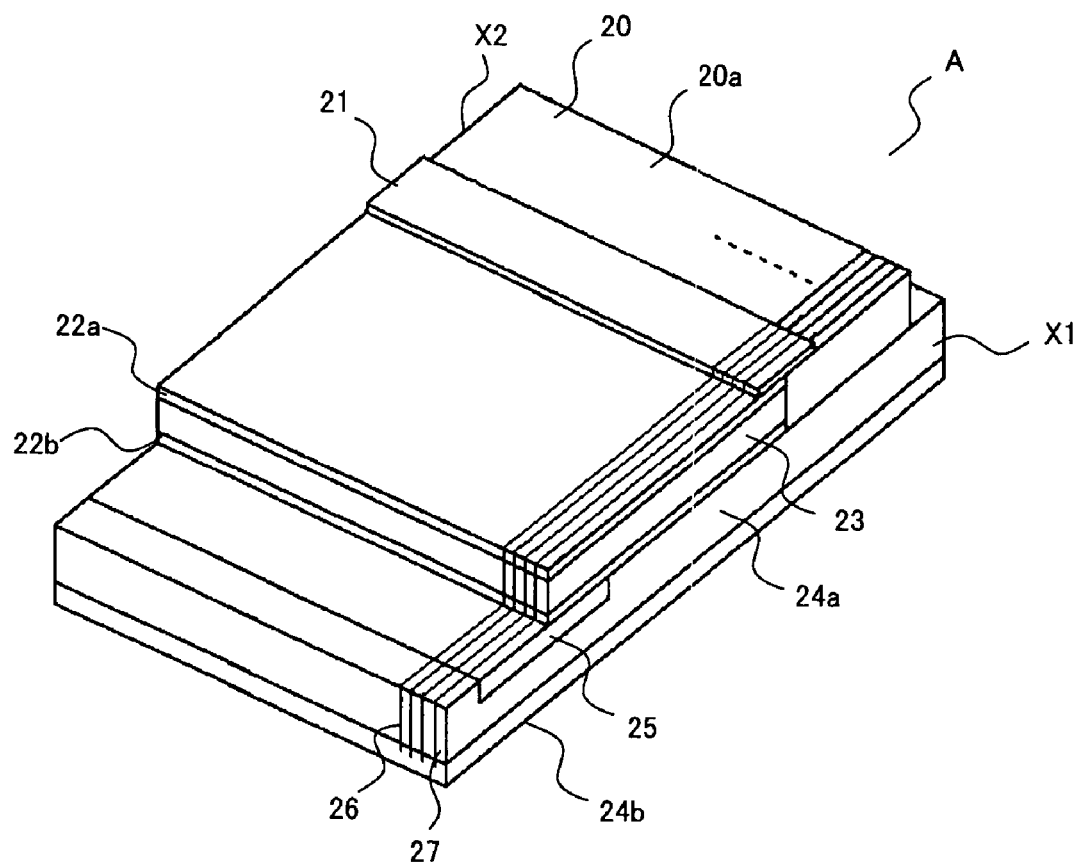
FIG. 3 is a perspective view of a structure configuring an piezoelectronic element transducer in a manufacturing process of the ultrasonic transducer.

FIG. 3 is a perspective view of a structure configuring an ultrasonic transducer in the manufacturing process of the ultrasonic transducer. In this figure, a structure A, which is configured with a wiring board 20, a conductor 21, electrodes 22 (22a, 22b), piezoelectric device 23, an acoustic matching layer 24 (first acoustic matching layer 24a, second acoustic matching layer 24b), a GND (Ground) conductor 25, and grooves 26, is initially manufactured when the ultrasonic transducer is formed. The manufacturing of the structure A is described.

Initially, the first acoustic matching layer 24a is formed after the second acoustic matching layer 24b is formed. Next, grooves are formed in the first acoustic matching layer 24a, for example, with a dicing saw (precise cutter), and conductive resin is poured in the grooves, so that the GND conductor 25 is formed. Then, the piezoelectric device 23 having opposed surface on which electrode layers 22a, 22b are respectively formed is glued. Next, the wiring board 20 is installed contiguously to the piezoelectric transducer 23. On the surface of the wiring board 20, an electrode layer 20a is formed. Then, the conductor 21 for electrically conducting the electrodes 20a and 22a is connected.

The above formed structure A is cut with the dicing saw, and a plurality of grooves (dicing grooves) 26 having a width of several tens of μm are formed. Preferably, the width of a groove is 20 to 50 μm. At this time, the structure A is cut so that only the second acoustic matching layer 24b is not perfectly cut to leave several tens of μm uncut.

Thereafter, processing according to the type of an ultrasonic transducer, such as a convex type, a linear type, a radial type, etc, is performed. For example, in the case of FIG. 2, this ultrasonic transducer is an ultrasonic transducer of an electronic radial type. Therefore, the structure A is formed to be cylindrical by making the both sides X1 and X2 of the structure A opposed.

Preferred embodiments are hereinafter described.

FIRST PREFERRED EMBODIMENT

This preferred embodiment refers to an ultrasonic transducer where the amount of a conductive adhesive on each piezoelectric transducer is made uniform, and the upper surface of a printing board, which is contiguous to the piezoelectric transducer, is positioned lower than the upper surface of the piezoelectric transducer.

FIG. 4 shows the manufacturing process of an ultrasonic transducer configuring the inside of the ultrasonic transducer 10 in this preferred embodiment. Initially, as described above, an acoustic matching layer 24 is formed, and a piezoelectric device 23 is glued onto the acoustic matching layer 24. Additionally, a wiring board 20 is glued to the upper surface of the acoustic matching layer 24 and a side of the piezoelectric transducer 23 (FIG. 4(a)). At this time, the thickness of the wiring board 20 is made thinner than that of the piezoelectric transducer 23 so that the upper surface of the wiring board 20 is not higher than the upper surface of the piezoelectric transducer 23. In this figure, electrode layers 22a, 22b are not shown. The same is applied also to FIGS. 5 to 7 to be described below.

Figure 4A:
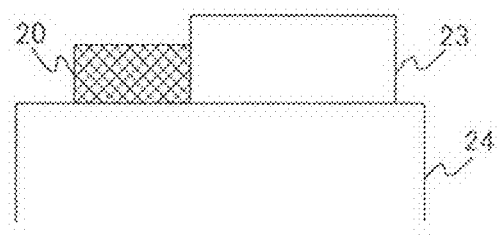
FIG. 4 is a schematic showing a manufacturing process of an ultrasonic transducer configuring the inside of an ultrasonic transducer 10 in the first preferred embodiment.
Figure 4B:
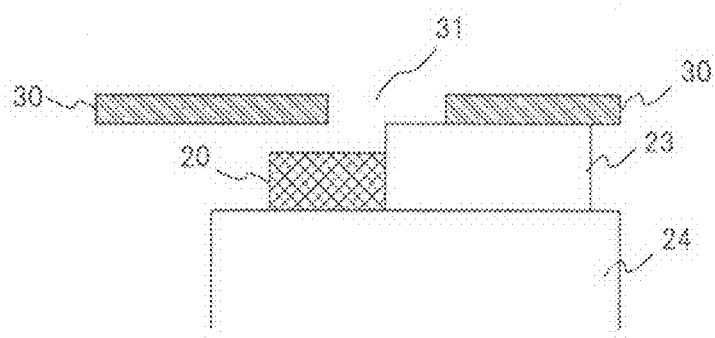

Next, a conductive adhesive 33 is printed with screen printing in order to electrically connect the piezoelectric device 23 and the wiring board 20. Namely, as shown in FIG. 4(b), a mask material 30 is initially made to contact the upper surface of the piezoelectric device 23. The mask material 30 used in this preferred embodiment is a flat plate, on which a slit 31 is provided in a plane direction. Since the upper surface of the wiring board 20 is lower than that of the piezoelectric device 23 as described above, a gap occurs between the lower surface of the mask 30 and the upper surface of the wiring board 20.

Figure 4C:
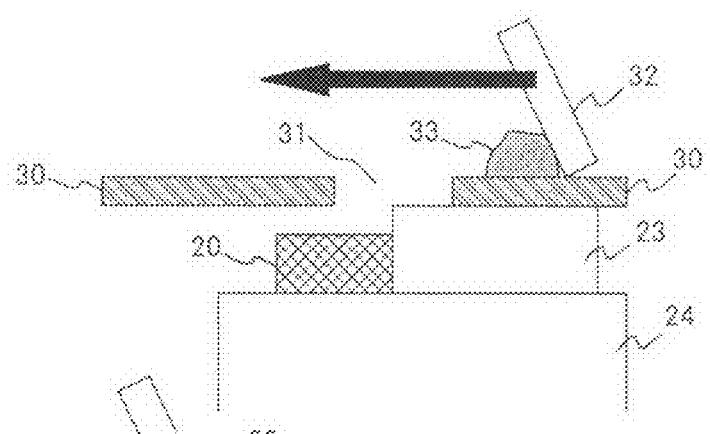
Figure 4D:
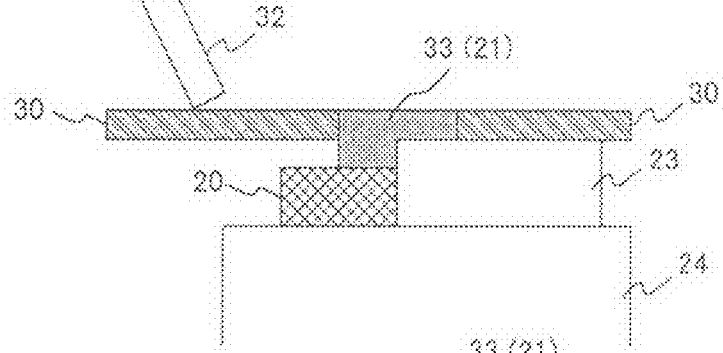

Next, as shown in FIG. 4(c), the conductive adhesive 33 is droped in the neighborhood of the slit 31 on the upper surface of the mask 30, and the end of a squeegee 32 is moved toward the slit 31 while being made to contact the upper surface of the mask 30. As a result, as shown in FIG. 4(d), the conductive adhesive 33 is pasted into the slit 31, and the conductive adhesive 33 is glued to the piezoelectric transducer 23 and the wiring board 20 in a shape along the shape of the slit 31 (namely, a conductor 21 is formed).

Figure 4E:
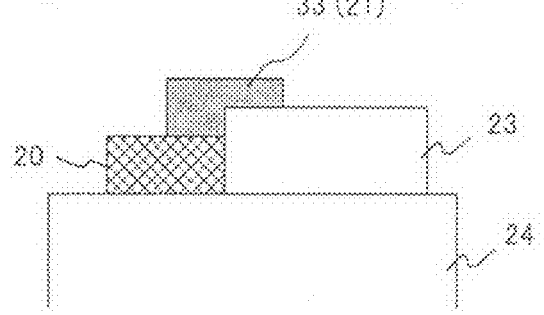

Thereafter, as shown in FIG. 4(e), the mask 30 is removed and heated, whereby the conductive adhesive 33 is harden. The conductive adhesive 33 is in a gel state, and its viscosity is high. Therefore, the conductive adhesive 33 never drips after the mask 30 is removed.

As described above, the lower surface of the mask 30 contacts the piezoelectric device 23 in all cases, and the amount of the conductive adhesive is fixed uniquely with the thickness of the mask 30 and the slit 31 of the mask 30. Therefore, the amount of the conductive adhesive 33 on each piezoelectric transducer 23 becomes uniform. Additionally, since the mass load of the conductive adhesive 33 on each piezoelectric element 23 becomes equal, a vibration characteristic (ultrasonic performance) becomes uniform. Accordingly, unevenness of the quality of an ultrasonic diagnostic image can be suppressed.

Incidentally, it is difficult to make the thickness of the wiring board 20 equal to that of the piezoelectric device 23 with precision in terms of mechanical processing. Even if a matching is made in terms of a designed size, a difference surely occurs on a tolerance level. If the wiring board 20 becomes thicker than the piezoelectric device 23, a gap between the piezoelectric device 23 and the mask 30 occurs. Therefore, the mask is deformed unintentionally by the squeegee 32, the amount of the conductive adhesive on each piezoelectric element 23 becomes indefinite, and the mass load becomes uneven for each element. In this preferred embodiment, the thickness of the wiring board 20 is made thinner than that of the piezoelectric device 23. Substantially, it is sufficient that the upper surface of the wiring board 20 is positioned lower than that of the piezoelectric transducer 23.

SECOND PREFERRED EMBODIMENT

This preferred embodiment refers to an ultrasonic transducer where the adhesion force of an adhesive is improved by increasing a surface area glued with the conductive adhesive.

Figure 5A:
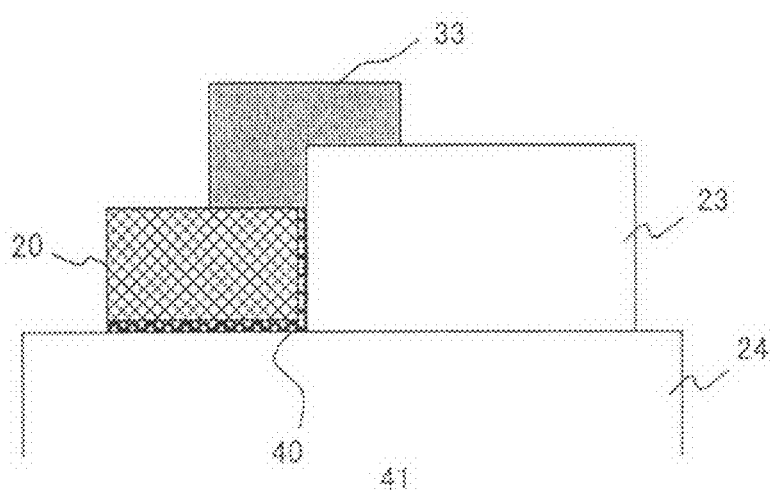
FIG. 5 is a schematic showing a manufacturing process of an ultrasonic transducer configuring the inside of an ultrasonic transducer 10 in the second preferred embodiment.

FIG. 5 shows the manufacturing process of an ultrasonic transducer configuring the inside of the ultrasonic transducer 10 in this preferred embodiment. As described in the first preferred embodiment, a wiring board 20 is glued to the upper surface of an acoustic matching layer 24 and a side of a piezoelectric transducer 23. This gluing is made with an adhesive 40 (FIG. 5(a)).

As described above, dicing grooves 26 are formed by making a plurality of cuts in a structure A with a dicing saw. If the structure A is not sufficiently bonded with the adhesive 40, the wiring board 20, the acoustic matching layer 24 or the piezoelectric device 23 comes off when the dicing grooves 26 are formed, possibly leading to a disconnection or a poor connection.

Figure 5B:
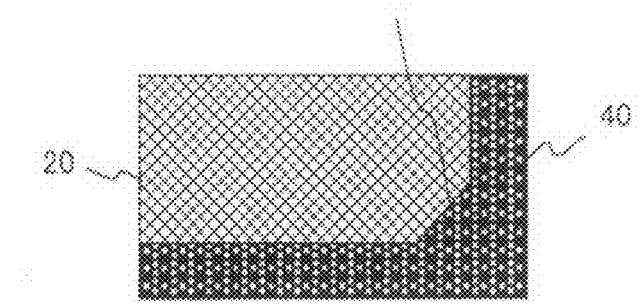
Figure 5C:
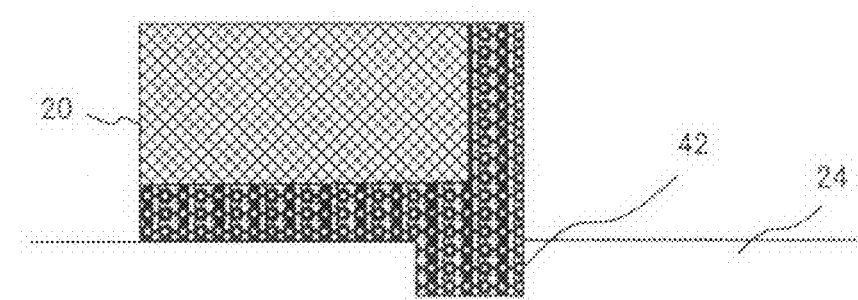

Accordingly, to improve the adhesion strength implemented by the adhesive 40, beveling (41) is made for an angle of the wiring board 20, thereby increasing the surface area to be glued as shown in FIG. 5(b). Additionally, as shown in FIG. 5(c), a concave part 42 is provided for the acoustic matching layer 24, and the adhesive is filled therein, whereby the surface area to be glued may be increased and an anchor effect may be expected. Additionally, FIGS. 5(b) and 5(c) may be combined.

Furthermore, as the adhesive, it is better to use, for example, an elastic adhesive. This is because using the elastic adhesive can prevent a bonded material from coming off due to vibrations. Additionally, using the elastic adhesive can suppress the hindrance of propagation of vibrations to a minimum on a boundary face between the adhesive and the bonded material.

As a result, the anchor effect of the adhesive is improved, and the mechanical and/or thermal load imposed when the wiring board is diced can be endured with a margin. This can improve a process yield.

Furthermore, as a modification example, the material of the wiring board may be made the same as the piezoelectric device, and a load on a dicing blade may be made equal.

THIRD PREFERRED EMBODIMENT

This preferred embodiment refers to an ultrasonic transducer which improves bonding between a conductive adhesive and a piezoelectric transducer by beveling an angle of the piezoelectric device 23.

FIG. 6 shows the manufacturing process of an ultrasonic transducer configuring the inside of the ultrasonic transducer 10 in this preferred embodiment. In this figure, beveling (50) is made for an angle of the piezoelectric device 23. The reason why such beveling is made is that an increase in an area between a conductive adhesive and the piezoelectric transducer can enhance the bonding of the conductive adhesive and the piezoelectric transducer.

Additionally, if the piezoelectric transducer vibrates in upward and downward directions, stress concentrates on the angle (acute angle portion) of the piezoelectric transducer, so that the conductive adhesive can come off from the piezoelectric transducer 23, and a disconnection can possibly occur. To avoid such a disconnection, the acute angle is beveled to scatter the stress.

As described above, the area where the conductive adhesive and the piezoelectric transducer contact increases, and the stress is scattered, whereby the ratio of a disconnection, etc. can be reduced to improve a process yield.

FOURTH PREFERRED EMBODIMENT

This preferred embodiment refers to an ultrasonic transducer which suppresses unnecessary vibrations other than those in upward and downward directions.

Figure 7A:
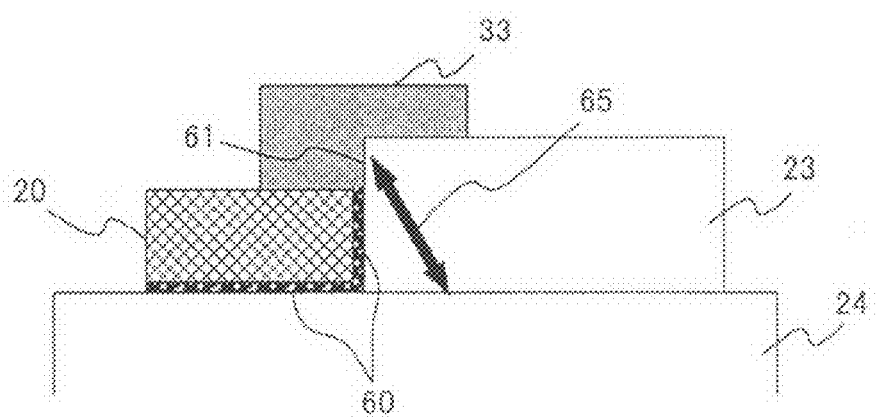
FIG. 7 is a schematic showing a state where an adhesive is coated on a side of a piezoelectric transducer 23 in the fourth preferred embodiment.
Figure 7B:
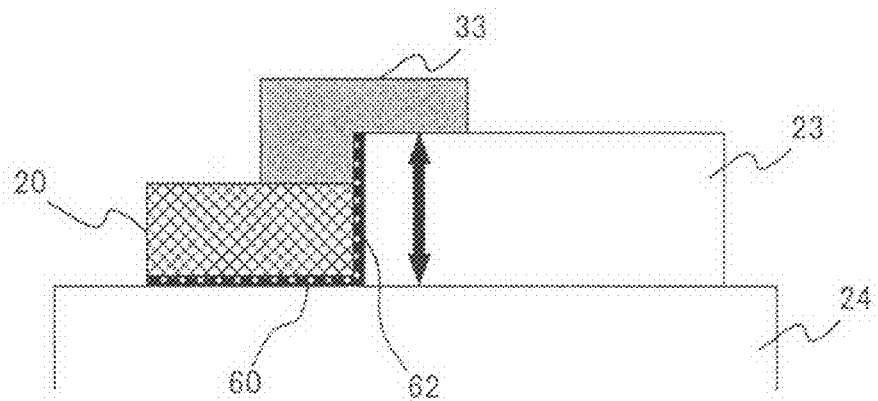

FIG. 7 shows a state where an adhesive is coated on the side of a piezoelectric device 23. FIG. 7(a) shows a case where the adhesive 60 is pasted only on the side of the piezoelectric device 23, which corresponds to a portion bonded to the side of a wiring board 20. FIG. 7(b) shows a case where the adhesive 62 is pasted on the entire side of the piezoelectric device 23.

An electric field occurs in upward and downward directions if a voltage is applied to the piezoelectric transducer, and vibrations in the same directions as the electric field occur. Originally, it is preferable that an electric field occurs between the upper and the lower surfaces of the piezoelectric transducer 23, and vibrations are made only in the upward and the downward directions as described above.

However, since a portion 61 of the side of the piezoelectric transducer 23 directly contacts the conductive adhesive 33 in FIG. 7(a), an electric field occurs also in an oblique direction between the side 61 and the bottom of the piezoelectric transducer 23 as indicated by an arrow 65. Therefore, vibrations occur in the same direction as this direction. Because the vibrations in this oblique direction are unnecessary vibrations, they can be a loss incurred for originally required vibrations. As a result, an acoustic characteristic degrades. Additionally, as vibrations propagating to the conductive adhesive 33, not only the vibrations in the upward and the downward directions but also the unnecessary vibrations propagate. The conductive adhesive 33 can be possibly distorted and cracked against such vibrations as described above, propagating in directions different from each other.

Furthermore, if different materials (the adhesive 60 and the conductive adhesive 33) contact on the same side of the piezoelectric transducer, the propagation state of vibrations differs when the piezoelectric transducer vibrates. This also leads to hindrance to the vibrations.

Therefore, as shown in FIG. 7(b), the adhesive 62 is coated on the entire side of the piezoelectric transducer 23. As a result, a portion of the side of the piezoelectric transducer 23 does not directly contact the conductive adhesive 33, and accordingly, the number of materials contacting the side 61 results in only one, and an acoustically discontinuous surface is eliminated. Therefore, unnecessary vibrations can be prevented from occurring from the side.

At this time, preferably, an elastic adhesive is used as the adhesive as described in the second preferred embodiment. Additionally, it is preferable that the elastic material is more insulative from a viewpoint of preventing an unnecessary electric field from occurring.

In the first to the fourth preferred embodiments, these embodiments may be combined. Additionally, the elastic adhesive may be used in any of the first to the fourth preferred embodiments.

As described above, an unnecessary electric field can be prevented from occurring by coating the entire side of the piezoelectric transducer with the elastic adhesive, whereby the generation of unnecessary vibrations can be eliminated. Additionally, vibrations to the conductive adhesive can be regulated, whereby an excess load is not imposed on the conductive adhesive. As a result, the conductive adhesive can be prevented from being cracked, leading to an improvement in a process yield.

As described above, the present invention is used, whereby an ultrasonic transducer of a small size, which does not hider an improvement in reliability and the vibrations of a piezoelectric transducer, can suppress variations in the characteristic.

The invention claimed is:

1. An ultrasonic transducer, which is configured with a plurality of piezoelectric elements having electrodes respectively on two opposed surfaces, an acoustic matching layer stacked on a side of a first surface that is one of the two surfaces, a wiring board which contacts a surface being in a direction perpendicular to the two surfaces of the piezoelectric element and is stacked on the acoustic matching layer in parallel with the piezoelectric element, and a conductor for electrically connecting the wiring board and the electrode on a side of a second surface that is one of the two surfaces, wherein
   a thickness of the wiring board is less than a thickness of the piezoelectric element, the thickness of the piezoelectric element being a dimension perpendicular to the second surface of the piezoelectric element.

2. The ultrasonic transducer according to claim 1, wherein the conductor is formed with uniform volume and mass for all of pairs each paring the piezoelectric element with the wiring board.

3. The ultrasonic transducer according to claim 1, wherein for surfaces of materials, such as the wiring board, the piezoelectric element and the acoustic matching layer, on which an adhesive is coated to adhere the materials, the adhesive is filled in a space provided at least in a portion of the surfaces of any of the materials.

4. The ultrasonic transducer according to claim 1, wherein an angle of the piezoelectric element is beveled and is covered by the conductor.

5. The ultrasonic transducer according to claim 1, wherein an adhesive for bonding materials such as the wiring board, the piezoelectric element and the acoustic matching layer is an elastic adhesive.

6. The ultrasonic transducer according to claim 1, wherein an elastic adhesive is coated on a portion where a side of the piezoelectric element and the conductor contact.

7. An ultrasonic endoscope comprising the ultrasonic transducer according to claim 1.

* * * * *